United States Patent [19]
Ochnio et al.

[11] Patent Number: 5,792,605
[45] Date of Patent: Aug. 11, 1998

[54] ASSAY FOR HEPATITIS A VIRUS SPECIFIC ANTIBODIES

[76] Inventors: Jan J. Ochnio, 4541 198th Street, Langley, B.C., Canada, V3A 1E7; Leslie Ann Mitchell, 568 Seashell Drive, South Delta, B.C., Canada, V4L 2K8

[21] Appl. No.: 675,783

[22] Filed: Jul. 5, 1996

[51] Int. Cl.$^6$ .................................................. C12Q 1/70
[52] U.S. Cl. .................. 435/5; 435/4; 435/7.92; 435/7.95
[58] Field of Search ................ 435/5, 4, 7.92, 435/7.95

[56] References Cited

FOREIGN PATENT DOCUMENTS

WO88/07680  10/1988  WIPO .

OTHER PUBLICATIONS

Delem, A., Vaccine 11(4): 479–484, 1993.
Macy et al., "Enhanced ELISA: how to measure less than 10 picograms of a specific protein (immunoglobulin) in less than 8 hours", The FASEB Journal, vol. 2, pp. 3003–3009, Nov. 1988.
Parry, et al., "Sensitive assays for viral antibodies in saliva: an altrnative to tests on serum", The Lancet, Jul. 11, 1987, 72–75.

Primary Examiner—Michael P. Woodward
Assistant Examiner—Brenda G. Brumback
Attorney, Agent, or Firm—Bell, Boyd & Lloyd

[57] ABSTRACT

A new, ultrasensitive, capture EIA based assay—ml-HAV EIA suitable for the detection of vaccine or disease-inducted Hepatitis A virus specific antibodies of IgG class in saliva. The method provides 99% sensitivity and specifically in comparison with serum based assays, and comprises a method of assaying specific immunoglobulin of any or all classes present in a human or animal bodily fluid selected from saliva, tears, semen, urine and cerebro spinal fluid by the steps of:

(i) immobilising an antibody to one or more classes of immunoglobulin onto a solid substrate;

(ii) exposing the immobilised antibody to a sample of said bodily fluid so as to achieve binding of a proportion of any immunoglobulin present in the fluid to said immobilised antibody;

(iii) exposing said bound immunoglobulin to a selected antigen so as to achieve binding of said antigen to at least a proportion of said bound immunoglobulin;

(iv) binding an antibody having specificity for said selected antigen to at least a proportion of said bound antigen; and (v) detecting and/or measuring said bound antibody having selected antigen specificity with a detecting antibody.

6 Claims, 1 Drawing Sheet

ASSAY FOR HEPATITIS A VIRUS SPECIFIC ANTIBODIES

FIELD OF THE INVENTION

This invention relates to methods of assay of immunoglobulin in saliva bodily fluid and particularly to a method of determining quantiatively the presence or amount of Hepatitis A virus specific IgG antibodies in saliva specimens.

BACKGROUND OF THE INVENTION

Recently, there has been considerable research interest in saliva as a much more amenable diagnostic medium than blood for evaluation of humoral immunity to a number of infectious agents (1–7). Testing of saliva for infectious agent-specific antibodies of IgG class immunoglobulin is especially useful in antibody surveys, particularly in children or others with high level of reluctance to participate in investigations requiring blood collection. Hepatitis A virus (HAV) was among the first infectious agents for which saliva-based assays (RIAs) assessing virus-specific antibodies of IgG and IgM class were established (1,8). Evaluation of anti-HAV antibodies by these "capture" RIAs in whole saliva was reported to be accurate in Hepatitis A diagnosis and in the differentiation between HAV immune and susceptible individuals, provided the immunity was established in the course of wild HAV infection (9,10). Successful Hepatitis A diagnosis with modified, serum-based assays which were subsequently applied to oral fluid samples collected with devices stimulating transsudation of immunoglobulin to oral fluid was also reported (5). However, these methods failed to detect with reasonable accuracy immunity induced by inactivated HAV vaccine (11,12) where serum anti-HAV levels are usually at least 10 times lower than those observed after HAV disease (13). Failure to detect lower levels of antibody precludes salivary monitoring of vaccine induced immunity and imposes some constrains also on the salivary evaluation of disease—induced immunity.

Salivary (oral fluid) antibodies of IgG class originate mainly in plasma and transude from capillaries in the tissue lining the gingival crevice. IgG concentration in crevicular fluid are much higher than in true saliva. Actual oral fluid concentrations of IgG fluctuate and are approximately 800–1000 fold lower than those found in serum (7,14,15, 16). Thus reliable evaluation of salivary specific antibody of IgG class requires an assay which is capable of sensitive detection of this antibody concentrations at least 1000 fold lower than those found in serum. Lack of sufficient sensitivity in most of immunoassays designed for serum antibody evaluation precludes their suitability for salivary antibody analysis. However, changes in the incubation time, specimen dilution factors, or ranges or reference curves improve the sensitivity of such methods. Also the use of specialized for collection of oral fluid devices such as "OraSure" wherein hypertonic solution induces increased transsudation of immunoglobulin to the mouth fluid can provide specimens with higher than usual IgG concentrations (17). This narrows to some degree the gap between specific antibody concentration in saliva specimen and serum making the saliva sample more suitable for analysis with assays originally designed for serum testing.

However, there is a need for an improved saliva based EIA for HAV specific IgG.

REFERENCE LIST

The present specification refers to the following publications, each of which is expressly incorporated herein by reference.

1. Parry J. V., Perry K. A., Mortimer P. P. Sensitive assays for viral antibodies in saliva: an alternative to tests on serum. Lancet 1987; July 11: 72–75.
2. Aiyar J., Bhan M. K., Bhandari N., Kumar R., Raj P., Sazawal S. Rotavirus-specific antibody response in saliva of infants with rotavirus diarrhea. J Inf Dis 1990: 162: 1383–4.
3. Parry J. V. Detection of viral antibodies in saliva as an alternative to serum. J Clin Chem Biochem 1989; 27(4): 245–247.
4. Perry K., Brown D., Parry J., Panday S., Pipkin C., Richards A. Detection of Measles, Mumps, and Rubella antibodies in saliva using antibody capture radioimmunoassay. J. Med. Virol. 1993; 40: 235–240.
5. Thieme T., Yoshihara P., Piacentini S. Beller M. Clinical evaluation of oral fluid samples for diagnosis of viral heptatis. J Clin Microbiol 1992; 30(5): 1076–1079.
6. Thieme T., Piacentini S., Davidson S., Steingart K. Determination of Measles, Mumps and Rubella immunization status using oral fluid samples. JAMA 1994; 272 (3): 219–221.
7. Parry J. V. Simple and reliable tests for HIV and Hepatitis A and B diagnosis and surveillance. In: Saliva as a diagnostic fluid. Annals of the New York Akademy of Sciences volume 694, 1993: 216–233 ed; Malamud D. and Tabak L.
8. Parry J. V., Perry K. R., Panday S., Mortimer P. P. Diagnosis of hepatitis A and B by testing saliva. J Med Vir 1989; 28: 255–60.
9. Parry J. V., Perry K. A., Mortimer P. P., Farrington C. P., Waight P. A., Miller E. Rational programme for screening travellers for antibodies to hepatitis A virus. Lancet 1988; June 25: 1447–9.
10. Parry J. V., Perry K. R., Panday S., Mortimer P. P., Diagnosis of hepatitis A and B by testing saliva, J Med Virol 1989; 28: 255–60.
11. Laufer D. S., Hurni W., Watson B., Miller W., Ryan J., Nalin D., Brown L. Saliva and serum as diagnosis media for antibody to Hepatitis A virus in adults and in individuals who have received an inactivated Hepatitis A vaccine. Clinical Infectious Diseases 1995; 20: 868–871.
12. Hurni W. M., Laufer D., Miller W. J., Ryan J., Watson B. Anti-hepatitis A in the general population and in Hepatitis A Vaccinees using saliva and serum as diagnostic media. In: Saliva as a diagnostic fluid. Annals of the New York Akademy of Sciences volume 694, 1993: 289–292 ed; Malamud D. and Tabak L.
13. Zaaijer H. L., Leentwaar-Kuijpers A., Rotman H., Lelie P. N. Hepatitis A antibody titers after infection and immunization. Journal of Medical Virology 1993; 40: 22–27.
14. Challacombe S. J., Russell M. W., Hawkes J. E., Bergmeier L. A., Lehner T. Passage of immunoglobulin from plasma to the oral cavity in rhesus monkeys. Immunology 1978; 39: 923–931.
15. Roitt I. M., Lehner T. Oral immunity. In: Immunology of oral diseases. 2nd ed., Oxford, Blackwell Scientific Publications, 1983: 279–304.
16. Bagg J., Perry K. R., Parry J. V., Mortimer P. P., Peters T. J. The influence of dental status on the detection of IgG class anti-viral antibodies in human saliva. Archs Oral Biol 1991; 36(3); 221–226.
17. Cordeiro M. L., Turpin, C. S., McAdams S. A. A comparative study of saliva and OraSure oral fluid. In: Saliva as a diagnostic fluid. Annals of the New York Akademy of Sciences volume 694, 1993 330–331 ed: Malamud D. and Tabak L.

18. Duermeyer W., van der Veen, J. Specific detection of IgM antibodies applied in hepatitis A. Lancet 1978; II: 684–685.
19. Macy E., Kemeny M., Saxon A. Enhanced ELISA: how to measure less than 10 picograms of a specific protein in less than 8 hours. FASEB 1988; 2: 3003–3009.

SUMMARY OF THE INVENTION

It is an object of the present invention to provide a new, ultra-sensitive EIA suitable for salivary evaluation of both vaccine—as well as disease-induced HAV-specific antibodies of the IgG class.

Since IgG antibody levels in saliva fluctuate according to the actual proportion of "true" saliva and crevicular fluid (7), the clinical usefulness of saliva-based test for HAV specific IgG depends on the assay's ability to differentiate between HAV immune and susceptible individuals rather than to measure exact concentrations of specific antibody in saliva. Nevertheless, the capture EIA for measurement of IgG class HAV-specific antibodies of the present invention has been calibrated against the World Health Organization International reference serum and has been shown to have lowest level of detectability around 0.0015 mIU/ml of specific IgG. The semiquantitative assay format of the invention has been designed to differentiate between immune and non-immune samples rather than to be fully quantitative.

The EIA of the invention is based on the principle of "capture" assay, where class specific antibody, coated on the solid phase, immobilises the representation of given class antibody from tested specimen. The amount of subsequently bound antigen indicates proportion of specific antibody present in the captured representation. This principle was successfully applied to the measurement of HAV specific antibodies in the serum in late seventies (18). It was also utilised by Parry in the RIAs designed to detect specific antibodies of the IgG or IgM class in saliva (1). These RIAs, although accurate in detection of salivary HAV-specific IgG in cases with disease induced immunity, were not sufficiently sensitive to detect lower levels of specific IgG in vaccinees. The inadequacy of these assays for salivary antibody determination was particularly evident in samples where corresponding serum levels of the same class specific anti-HAV were lower than 9,000 mIU/ml (as in the majority of vaccinees) (11, 12).

Accordingly, in one aspect, the invention provides a method of assaying specific immunoglobulin of any or all classes present in a human or animal bodily fluid selected from saliva, tears, semen, urine and cerebro spinal fluid by the steps of:

(i) immobilising an antibody to one or more classes of immunoglobulin onto a solid substrate;

(ii) exposing the immobilised antibody to a sample of said bodily fluid so as to achieve binding of a proportion of any immunoglobulin present in the fluid to said immobilised antibody;

(iii) exposing said bound immunoglobulin to a selected antigen so as to achieve binding of said antigen to at least a proportion of said bound immunoglobulin;

(iv) binding an antibody having specificity for said selected antigen to at least a proportion of said bound antigen; and (v) detecting and/or measuring said bound antibody having selected antigen specificity with a detecting antibody.

In a further aspect, the invention provides a kit for assaying specific immunoglobulin of any or all classes present in a human or animal bodily fluid selected from saliva, tears, semen, urine and cerbrospinal fluid using the method as hereinabove defined wherein the kit contains one or more of the reagents necessary for performing one or more of steps (i)–(v).

The method of the invention is particularly of value wherein the immunoglobulin is IgG or IgM and wherein the immunoglobulin to be assayed is produced in response to infection by Hepatitis A, Hepatitis B, Human Immunodeficiency Virus, Rubella, Measles, Mumps, Human Parvovirus B19 or Chickenpox (VZ virus).

The method of the invention is particularly valuable wherein the fluid is saliva obtained from a patient, which saliva may be used either undiluted or diluted but without a step of increasing the immunoglobulin concentration.

When the immunoglobulin to be assayed is provided in response to infection by Hepatitis A the selected antigen is HAV antigen and the antibody having said specificity for said selected antigen is a highly-specific murine anti-HAV monoclonal antibody.

The detecting antibody is most preferably an enzyme conjugated polyclonal anti-mouse IgG or alternatively radiolabelled.

BRIEF DESCRIPTION OF THE DRAWING

In order that the invention may be better understood, a preferred embodiment will now be described by way of example only with reference the following drawings wherein:

FIG. 1 is a pictorial representation of an immunoassay according to the prior art;

FIG. 2 is a pictorial representation of an alternative immunoassay according to the prior art;

FIG. 3 is a pictorial representation of an immunoassay according to the invention; and wherein:

Figures 1, 2, 3:
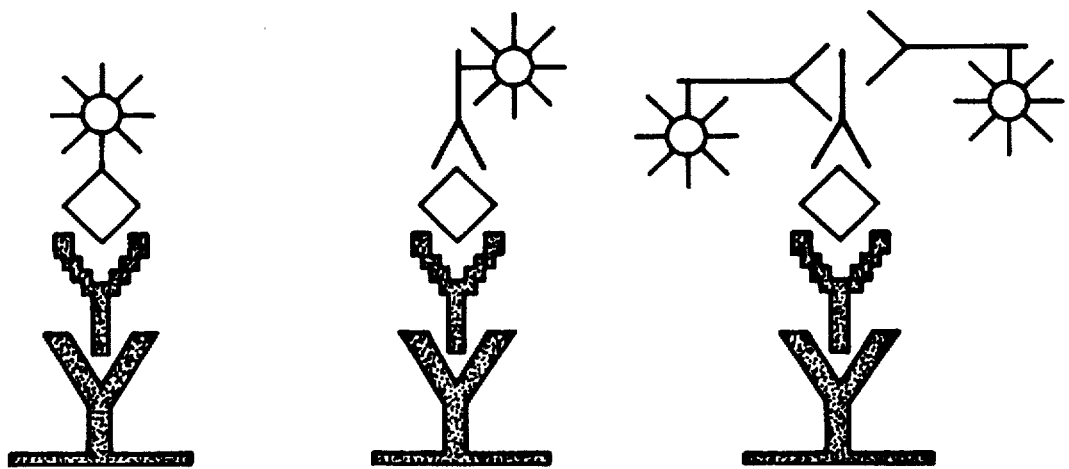

| Y "capture" antibody | Y anti-HAV murine monoclonal |
|---|---|
| Y anti-HAV IgG from sample | Y polyclonal anti-mouse |
| ◊ HAV antigen | ✱ label (enzyme or radioisotope) |

DETAILED DESCRIPTION OF A PREFERRED EMBODIMENT

Although the EIA of the present invention and the former capture RIA (1) as well as other serum based EIAs utilise the same general principle, the format of the EIA of the invention has been designed to afford the enhanced sensitivity required for detecting the anticipated very low levels of HAV-specific IgG in saliva from vaccines. This requires two additional steps which make this EIA distinct from already available immunoassays: first instead of using enzymatically or radioisotopically) labelled HAV antigen (FIG. 1) or labelled in the same manner HAV-specific detecting antibody (FIG. 2), the EIA presented here employs a three-layer antibody detection system. This includes: unlabelled HAV antigen, followed by a highly-specific murine anti-HAV monoclonal antibody which is subsequently detected by enzyme conjugated polyclonal anti-mouse IgG (FIG. 3). Sensitivity is further enhanced by the use based on tetrazolium reduction by NADH ELISA amplification system (19).

METHODS

Study Subject:

Study subjects included 91 adult participants of Hepatitis A vaccine trial in whom paired samples were obtained four weeks after the third dose of inactivated HAV vaccine (SmithKline Beecham), 1025 international travellers seeking immunization advice at Vancouver Health Department travel clinics representing a broad range of ages and ethnic backgrounds and 134 volunteers (69 adult and 65 teenage) who agreed to participate in this study. All subjects had negative history of immunoglobulin administration or blood transfusion within six months before the onset of the study. With the exception of participants in the HAV vaccine trial, all remaining subjects had a negative history for Hepatitis A vaccination.

Specimen Collection:

Paired saliva and serum samples were collected from all study participants. Vaccines and 22 volunteers produced full saliva sample by salivating directly into the large opening tubes. Saliva selection in travellers and remaining 112 volunteers was facilitated by the use of Salivate with neutral insert (Sarstedt, Inc., Germany). All salivary and serum specimens were aliquotted and frozen at −70 C. until tested.

Determination of HAV-specific antibodies in serum samples:

All sera collected from travellers were screened for the presence of total anti-HAV by Abbott HAVAB IMX at the Virology Laboratory at the B.C. Center for Disease Control (BCCDC, Vancouver, B.C.). Sera from volunteers and from vaccinees were tested in the Vaccine Evaluation Center Laboratory for total anti-HAV using the Heptrofile Anti-HAV (ADI Diagnostics). Positive results obtained with Heprofiled were confirmed by comparison of tests on the same sera using HAVAB IMX or by measuring total anti-HAV content by RIA (Abbott) as it was the case in all specimens from vaccinees.

Determination of HAV specific IgG antibodies in saliva specimens:

All saliva samples were tested for HAV specific IgG antibodies with the capture enzymeimmunoassay (EIA) according to the invention.

To capture human anti-HAV, first the wells of 96 well, flat bottom polystyrene microplates (Immulon 2, Dynatech Inc., Chasiyilly, Va.) were coated overnight at room temperature with F(ab)2 fragments of donkey anti-human IgG (Jackson Immuno Research Laboratories, West Grove, Pa.) 1.2 ug/ml in carbonate/bicarbonate buffer pH 9.6. The wells were subsequently blocked for 1 hour at room temperature with 1% bovine serum albumin (BSA) in phosphate buffer saline (pH 7.4) contining 0.05% (v/v) Tween 20 (PBS-T). For each specimen tested, four wells were allocated. Saliva specimens, diluted 1:4 in PBS-T containing 0.5% BSA, were incubated on the plate for 1.5 hour to allow capture of IgG class antibody representation. Of wells devoted for each specimen two subsequently received HAV antigen (SmithKline Beecham, Rixensart, Belgium) diluted to 432 ELU/ml in PBS-T containing 0.5% BSA while the remaining two received buffer only to serve as an antigen negative control wells for non-specific binding. This overnight incubation allowed for antigen binding, provided HAV—specific antibody was present in captured representation of IgG from saliva. To detect bound specific antibodies all microplate wells subsequently received 0.025 ug/ml dilution (in PBS-T containing 0.5% BSA) of HAV specific monoclonal antibody (Clone K3.4C8, Commonwealth Laboratories, Parkville, Australia). This 1.5 hour incubation was followed by exposure of all wells also for one hour and a half to alkaline phosphatase (AP)-conjugated F(ab)2 fragments of donkey anti-mouse IgG (H+L)(Jackson Immuno Research Laboratories, West Grove, Pa.) diluted to 0.2 ug/ml in PBS-T containing 0.5% BSA. The amount of bound AP-conjugated was then determined spectrophotometrically using ELISA amplification system (Life Technologies, Inc. Gaithersburg, Md.). This signal enhancing, based on the reduction of iodonitrotetrazolium by NADH method was used according to manufacturer's instructions and required 15 min. incubation with substrate. When absorbance at 490 nm (A490) in the positive control wells reached 1.4 amplification phase was stopped by addition of 0.3M sulphuric acid to each well.

All incubations were conducted at room temperature and were separated by extensive washing of the wells with PBS-T at the end of each incubation what led to the removal of unbound elements. Washing was facilitated by LP 35 washer (Pasteur Diagnostics . . . France). PBS-T was substituted with 0.05 molar TRIS/HCl buffer pH 7.5 in the last washing which followed incubation with AP-conjugate.

For each specimen tested, the ratio of absorbance observed in wells exposed to HAV to the absorbance from control wells was calculated. A sample was considered to be positive for HAV specific IgG if the ratio exceeded the cut off value equal to mean plus 2 SD of ratios determined in salivary specimens obtained from 200 seronegative individuals.

RESULTS

Anti-HAV antibody in serum and saliva of HAV vaccinees:

All 91 HAV vaccine recipients were found to be seropositive for anti-HAV by both Heprofile and RIA. The lowest serum level observed in this group was 80 mIU/ml while the highest value was 35,100 mIU/ml of total virus specific antibody. Thirty of these vaccines (33%) exhibited serum levels greater than 6000 mIU/ml, while among remaining 61 vaccinees, 15 individuals had serum levels lower than 2,000 mIU/ml. Ninety one (100%) of the corresponding saliva samples from seropositive vaccinees were also found to be positive for HAV-specific antibody of IgG class.

Anti-HAV antibody in international travellers:

Of specimens obtained from 1026 travellers enrolled into the study, 1025 pairs were in sufficient volume for both saliva and serum testing. Of the 327 travellers who were found to be seropositive for total anti HAV, 325 (99.4%) tested positive for HAV-specific IgG in saliva. Among the 698 seronegative subjects salivary testing for HAV-specific IgG was negative in 689 cases. In the nine discrepant saliva samples observed signal to background ratios were however on positive side but close to the cut off point.

Anti-HAV antibody in volunteer subjects:

Among the 134 volunteers, 33 tested positive and 101 were negative for total anti HAV in serum. Only one disconcordant with serum salivary result observed. This occurred in seronegative individual who tested weakly positive for HAV-specific IgG in saliva.

In summary the results presented in Table 1 showed that 449 of 451 seropositive study subjects also had a positive salivary test, indicating a 99.6% sensitivity of our salivary assay for anti-HAV IgG in comparison with conventional, serum based total anti-HAV antibody determinations. Among 799 seronegative subjects, 789 showed negative in saliva test indicating a specificity of 98.8% for the salivary antibody EIA.

TABLE 1

HAV-specific antibodies in paired saliva and serum specimens.

| Number of individuals | Group of subjects | | | |
|---|---|---|---|---|
| | vac-cines* | travel-lers** | volun-teers*** | Total |
| seropositive[1] with positive saliva[2] | 91 | 325 | 33 | 449 |
| seropositive with negative saliva | 0 | 2 | 0 | 2 |
| seronegative with negative saliva | 0 | 689 | 100 | 789 |
| seronegative with positive saliva | 0 | 9 | 1 | 10 |
| Total | 91 | 1025 | 134 | 1250 |

[1]Total HAV-specific antibodies (IgG + IgM + IgA) were determined in serum.
[2]HAV-specific IgG antibodies in saliva were determined by presented capture EIA.
*Sample collected 4 weeks after administration of third dose of HAV inactivated vaccine.
**Attendees of Vancouver public health travel clinics.
***Volunteer participants from research institution staff members and/or participants in other vaccine trials.

The data shown in Table 1 indicate that saliva-based testing for IgG class HAV-specific antibody with the capture EIA is almost as accurate in identification of susceptible and immune individuals as conventional serum-based testing for total anti-HAV antibodies showing sensitivity and specificity of 96.6% and 98.8% respectively in tests of paired specimens from 1250 individuals showing broad range of specific IgG levels. Very few false positive results in comparison with serum based assay were observed. The few discrepancies might be explained by the fact that the serum base assays used in this study measure total anti-HAV (IgG+ IgM+IgA) while our EIA selectively detects IgG antibodies. Hence, these would likely be resolved if other class specific antibody levels were determined in saliva samples. False positive salivary results likely arise as a result of non-specific binding of the antigen to the saliva elements which non-specifically bind to the components used to capture class specific antibodies or might simply represent "false negatives" in serum based assay which was used for comparison. Although Parry also reported low levels of false positively and negativity in cases with immunity resulting from HAV disease (9) his salivary RIA identified substantial number of equivocal cases. The extreme sensitivity of the capture EIA of the present invention allows a clean cut distinction in such cases. But more importantly, this EIA is sensitive enough to detect accurately low levels of anti-HAV IgG induced by vaccination. Sensitive detection of anti-HAV in saliva was observed even in cases with very low corresponding serum antibody levels lower than 1 IU/ml.

In conclusion, the direct testing of ordinary (unstimulated) saliva samples for HAV specific IgG using the capture EIA according to the invention provides an useful alternative to serum-based assays for discriminating between Hepatitis A virus-immune and non-immune individuals. The convenience, accuracy and complete noninvasive nature of this methodology makes it an attractive tool in the rationale utilization of the newly available Hepatitis A vaccine not only for selection of non-immune candidates for vaccination, but also for monitoring of vaccine-induced immunity. Moreover, this assay may be effectively used in epidemiological surveys of the HAV immune status of the general population or selected high risk groups such as children attending day care, intravenous drug users, workers or homosexuals. More significantly, the capture EIA of the present invention will serve as a prototype for the future development of other assays for evaluation of antibody mediated immunity levels expressed at mucosal surfaces in other than HAV viral or bacterial pathogens.

While the invention has been described in detail and with reference to specific embodiments thereof, it will be apparent to one skilled in the art that various changes and modifications can be made therein without departing from the spirit and scope of the invention.

We claim:

1. A method of assaying Hepatitis A specific IgG antibodies present in a human or animal bodily fluid selected from saliva, tears, semen, urine and cerebrospinal fluid to a level of detectability of about 0.0015 mIU/ml of antibody by the steps of:

(i) immobilizing an anti-IgG antibody onto a solid substrate;

(ii) exposing the immobilised antibody to a sample of said bodily fluid so as to achieve binding of a proportion of any Hepatitis A specific IgG antibodies present in the fluid to said immobilised antibody;

(iii) exposing said bound sample IgG antibodies to a selected antigen so as to achieve binding of said antigen to at least a proportion of said bound sample IgG antibodies;

(iv) binding an antibody having specificity for said selected antigen to at least a proportion of said bound antigen; and (v) detecting and/or measuring said bound antibody having selected antigen specificity with a detecting labelled antibody to a level of detectability of about 0.0015 mIU/ml of antibody.

2. A method according to claim 1 wherein said fluid is saliva.

3. A method according to claim 2, wherein said saliva is obtained from a patient and then used either undiluted or diluted but without a step of increasing the IgG antibody concentration.

4. A method according to claim 1 wherein said antibody having said specificity for said selected antigen is a highly-specific murine anti-HAV monoclonal antibody.

5. A method according to claim 4 wherein said detecting labelled antibody is an enzyme conjugated polyclonal anti-mouse IgG.

6. A method according to claim 1 wherein said detecting and/or measuring step (v) is determined spectrophotometrically by using ELISA amplification system based on tetrazolium reduction by NADH.

* * * * *